United States Patent
Le Flohic et al.

(10) Patent No.: US 9,925,195 B2
(45) Date of Patent: Mar. 27, 2018

(54) SALT OF 3-[(3-{[4-(4-MORPHOLINYLMETHYL)-1H-PYRROL-2-YL]METHYLENE}-2-OXO-2,3-DIHYDRO-1H-INDOL-5-YL)METHYL]-1,3-THIAZOLIDINE-2,4-DIONE, ITS PREPARATION, AND FORMULATIONS CONTAINING I

(71) Applicant: LES LABORATOIRES SERVIER, Suresnes (FR)

(72) Inventors: Alexandre Le Flohic, Fauville en Caux (FR); Jérôme Guidotti, Criquetot sur Ouville (FR); Philippe Letellier, Orleans (FR)

(73) Assignee: LES LABORATOIRES SERVIER, Suresnes (FR)

( * ) Notice: Subject to any disclaimer, the term of this patent is extended or adjusted under 35 U.S.C. 154(b) by 0 days.

(21) Appl. No.: 14/904,260

(22) PCT Filed: Jul. 11, 2014

(86) PCT No.: PCT/FR2014/051783
§ 371 (c)(1),
(2) Date: Jan. 11, 2016

(87) PCT Pub. No.: WO2015/004395
PCT Pub. Date: Jan. 15, 2015

(65) Prior Publication Data
US 2016/0151378 A1    Jun. 2, 2016

(30) Foreign Application Priority Data

Jul. 12, 2013 (FR) .................... 13/56870

(51) Int. Cl.
C07D 417/14 (2006.01)
A61K 31/5377 (2006.01)
A61K 45/06 (2006.01)

(52) U.S. Cl.
CPC .......... *A61K 31/5377* (2013.01); *A61K 45/06* (2013.01); *C07D 417/14* (2013.01)

(58) Field of Classification Search
CPC .................................................. C07D 417/14
See application file for complete search history.

(56) References Cited

U.S. PATENT DOCUMENTS

| | | | |
|---|---|---|---|
| 8,133,889 B2 * | 3/2012 | Ortuno | C07D 401/12 514/235.2 |
| 8,541,412 B2 * | 9/2013 | Ortuno | C07D 401/12 514/235.2 |
| 8,653,073 B2 * | 2/2014 | Ortuno | C07D 401/12 514/235.2 |
| 2011/0034460 A1 * | 2/2011 | Ortuno | C07D 401/12 514/235.2 |

FOREIGN PATENT DOCUMENTS

EP    2281822    2/2011
WO    WO 2007/067495    6/2007

OTHER PUBLICATIONS

International Search Report for PCT/FR2014/051783 dated Oct. 23, 2014.

* cited by examiner

*Primary Examiner* — Matthew P Coughlin
(74) *Attorney, Agent, or Firm* — Hueschen and Sage

(57) ABSTRACT

3-[3-{[4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate of formula (II):

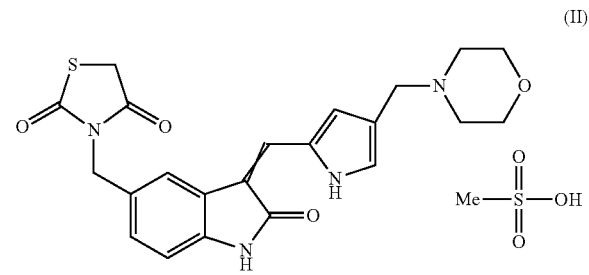

Medicinal products containing the same which are useful in treating cancer.

9 Claims, 1 Drawing Sheet

SALT OF 3-[(3-{[4-(4-MORPHOLINYLMETHYL)-1H-PYRROL-2-YL]METHYLENE}-2-OXO-2,3-DIHYDRO-1H-INDOL-5-YL)METHYL]-1,3-THIAZOLIDINE-2,4-DIONE, ITS PREPARATION, AND FORMULATIONS CONTAINING I

The present invention relates to a new salt of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione of formula (I):

(I)
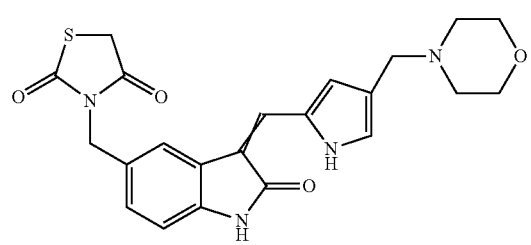

to its preparation process and also to pharmaceutical compositions containing it.

3-[(3-{[4-(4-Morpholinylmethyl)-1H-pyrrol-2-yl]methylene}-2-oxo-2,3-dihydro-1H-indol-5-yl)methyl]-1,3-thiazolidine-2,4-dione has very valuable pharmacological properties in the field of cancerology. It has in fact been shown that 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione has the ability to inhibit the migration of cancer cells, making it especially useful in the treatment of cancers and, more especially, solid metastatic tumours. Among the cancers envisaged for treatment there may be mentioned, without implying any limitation, cancers of the colon, breast, liver, kidneys, brain and œsophagus, melanomas, myelomas, ovarian cancers, non-small-cell lung cancers, small-cell lung cancers, prostate and pancreatic cancers, and sarcomas.

The preparation and therapeutic use of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione and its addition salts with a pharmaceutically acceptable acid, and more especially its hydrochloride, have been described, for example, in the European patent specification EP 2281822.

In view of the pharmaceutical value of this compound it is important to be able to obtain the active compound in excellent yields, with high purity and with excellent reproducibility. It was rapidly found that the hydrochloride which was used presented problems of purification and recrystallisation, and also a yield that was very difficult to optimise. Furthermore, problems of reproducibility and consistency of the active compound obtained were observed. After numerous research studies, it was possible to identify a new salt combining various advantages, especially relating to purification, to reproducibility of the process for obtaining it and to yield, but also unexpectedly having the advantage of very significantly improving the solubility of the active compound. This new salt accordingly has all the qualities indispensable to its use as a medicament, from both the physicochemical and the pharmacokinetic point of view.

The present invention accordingly relates to a new salt of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione, more especially 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate of formula (II):

(II)
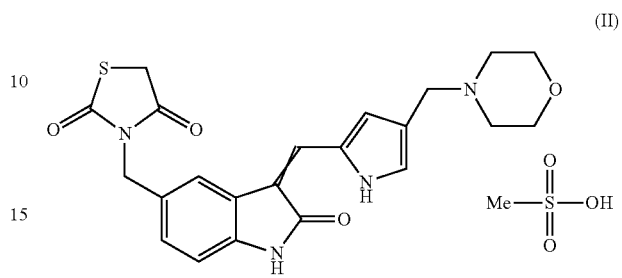

wherein the notation

⨯ means that the double bond is of configuration Z or E. The invention preferably relates to the Z isomer of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate.

This new salt has the following advantages:
a simple and reproducible process for obtaining it in an excellent yield;
increased solubility in both water and organic solvents, making it possible to envisage purification stages such as clarifications, in order to increase its purity.

The invention relates also to a process for obtaining 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate, more especially its Z isomer, characterised in that there is used as starting material 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione obtained for example in accordance with a process described in the patent specification EP 2281822. The dione is dissolved in a binary system of solvent/water, then from 1 to 2 molar equivalents of methanesulphonic acid are added and the mixture is stirred until the methanesulphonate precipitates out.

The solvent will advantageously be a polar solvent such as, for example, acetonitrile, acetone, 1,4-dioxane, tetrahydrofuran, N,N-dimethylformamide, N,N-dimethylacetamide, dimethyl sulphoxide, alcohols such as methanol, ethanol and isopropanol, water and also aqueous/organic mixtures of those solvents. Preferably, the solvent/water ratio will be 0/100 to 100/0.

A variant of the process according to the invention consists of using as starting material 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione hydrochloride; the manner in which this compound is obtained has been described, for example, in the patent specification EP 2281822. The hydrochloride is dissolved in a binary system of solvent/water, and the pH of the mixture is brought to 8 by adding a base. The salt formed is removed by filtration. The filtrate is heated and then methanesulphonic acid is added. The temperature is then slowly returned to ambient temperature, and the methanesulphonate obtained is filtered off. More especially, the solvent used is a polar solvent such as acetonitrile, acetone, 1,4-dioxane, tetrahydrofuran, N,N-dimethylformamide, N,N-dimethylacetamide, dimethyl sulphoxide, or alcohols such as methanol, ethanol and isopropanol. Preferably the solvent/water ratio will be 70/30 and, more especially, 90/10. The methanesulphonic acid is used in excess, more especially from 1 to 2 equivalents.

The compound of formula (II) according to the invention has excellent stability over time even under denaturing conditions: at 25° C./60% relative humidity, at 25° C./90% relative humidity, at 30° C./65% relative humidity, at 40° C./75% relative humidity, or at 50° C., the compound of formula (II) is unchanged after 6 months.

The invention relates also to pharmaceutical compositions comprising as active ingredient the compound of formula (II) according to the invention, more especially its Z isomer, together with one or more inert, non-toxic, appropriate excipients. Among the pharmaceutical compositions according to the invention there may be mentioned more especially those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

The pharmaceutical forms comprising the compound of formula (II) according to the invention, more especially its Z isomer, will be used in the treatment of cancers and, more especially, solid metastatic tumours. Among the cancers envisaged for treatment there may be mentioned, without implying any limitation, cancers of the colon, breast, liver, kidneys, brain and œsophagus, melanomas, myelomas, ovarian cancers, non-small-cell lung cancers, small-cell lung cancers, prostate and pancreatic cancers, and sarcomas.

The useful dosage can be varied according to the nature and severity of the disorder, the administration route and the age and weight of the patient. The dosage varies from 1 mg to 1 g per day, in terms of the base equivalent, in one or more administrations.

The Examples hereinbelow illustrate the invention but do not limit it in any way.

EXAMPLE 1

3-[(3-{[4-(4-Morpholinylmethyl)-1H-pyrrol-2-yl]methylene}-2-oxo-2,3-dihydro-1H-indol-5-yl)methyl]-1,3-thiazolidine-2,4-dione Methanesulphonate, Z Isomer 1.26 g of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione are introduced into a 100-mL flask. After adding 20 mL of a solution of acetonitrile/water (90/10), the mixture is heated at 70° C. A solution containing 2 mL of methanesulphonic acid and 50 mL of a mixture of acetonitrile/water (90/10) is prepared. 5 mL of the resulting solution are added to the reaction mixture, which becomes clear. The solution is cooled to 20° C. (0.5° C./min, stirring at 200 rpm). After stirring overnight at ambient temperature, the title product is isolated by filtration, and dried at 40° C. in vacuo (10 mbars).

Melting point: 270-274° C. (melting/decomposition)

The title product is characterised by its powder diffractogram, carried out on 50 mg of the compound of Example 1, placed between 2 Kapton® films or on a support and loaded into a Panalytical Xpert-Pro MPD diffractometer (copper anticathode) in transmission mode with an angular range of 3-55° in terms of 2θ, a step of 0.017° and 35.5 s per step, which makes it possible to identify the following crystal parameters:

unit cell parameters: a=15.0958(5) Å, b=18.4586(6) Å, c=8.8269(2) Å, β=94.074(1)°, γ=90° space group: C 1 c 1 (9)

volume of unit cell: $V_{unit\ cell}$=2453.37600 Å$^3$

The title product was also characterised by X-ray diffraction of a single crystal of the compound of Example 1, carried out with a Rigaku XtaLAB apparatus using graphite monochromatic Mo-Ka radiation. The following crystal parameters were observed:

unit cell parameters: a=14.995(4) Å, b=18.302(4) Å, c=8.850(2) Å, β=93.528(7)°, γ=90° space group: C 1 c 1 (9)

volume of unit cell: $V_{unit\ cell}$=2424.0 (9) Å$^3$

The slight differences observed in the parameters obtained using the powder are due to the temperature used to obtain the parameters with the single crystal (−100° C.), which causes a contraction along the axes a and b.

Figure 1:
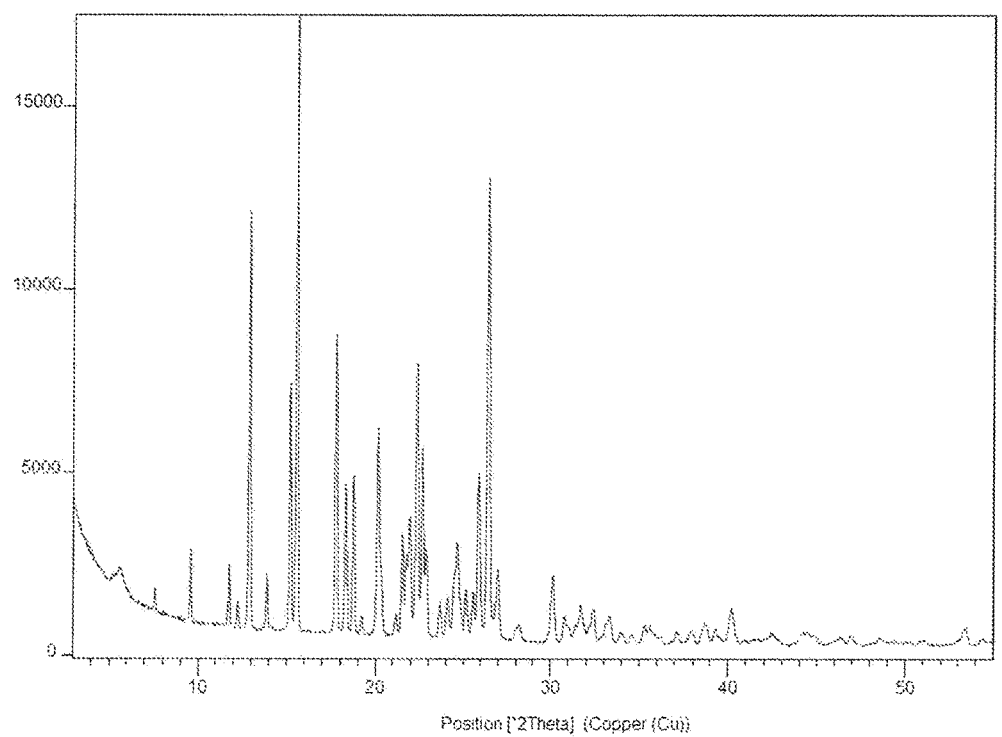
FIG. 1 shows the X-ray powder diffraction diagram for the compound of Example 1.

The title product was also characterised by its X-ray powder diffractogram shown in FIG. 1 and measured using a Panalytical XPert Pro MPD diffractometer (copper anti-cathode) and expressed in terms of interplanar distance d, Bragg's angle 2 theta (expressed in °±0.2) and relative intensity (expressed as a percentage relative to the most intense line):

| 2-Theta (°) exp. | d (Å) exp. | Intensity (%) |
| --- | --- | --- |
| 12.8678 | 6.87420 | 60.31 |
| 15.1323 | 5.85020 | 38.36 |
| 15.5005 | 5.71203 | 100.00 |
| 17.7050 | 5.00549 | 48.23 |
| 18.2579 | 4.85513 | 23.89 |
| 18.7110 | 4.73856 | 25.22 |
| 20.1109 | 4.41177 | 30.15 |
| 21.4617 | 4.13704 | 16.97 |
| 21.6776 | 4.09632 | 15.77 |
| 21.8970 | 4.05576 | 15.98 |
| 22.2971 | 3.98390 | 41.52 |
| 22.5852 | 3.93372 | 38.20 |
| 24.5702 | 3.62023 | 17.23 |
| 25.8231 | 3.44735 | 24.17 |
| 26.3301 | 3.38211 | 83.15 |

Bragg's angles 2-theta (expressed in °±0.2) characteristic of the X-ray powder diffractogram: 12.86; 15.13; 15.50; 17.70; 18.25; 18.71; 20.11; 21.46; 21.67; 21.89; 22.29; 22.58; 24.57; 25.82; 26.33.

The compound of Example 1 was also characterised by its DSC diagram, for a sample of 5-10 mg loaded into a TA Instruments DSC Q1000 apparatus and cooled to 0° C. The sample is then heated to 300° C. at a rate of 10° C./min. The diagram obtained is shown in FIG. 2.

EXAMPLE 2

Purity and Stability of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione Methanesulphonate, Z Isomer, Under Denaturing Conditions

Figure 2:
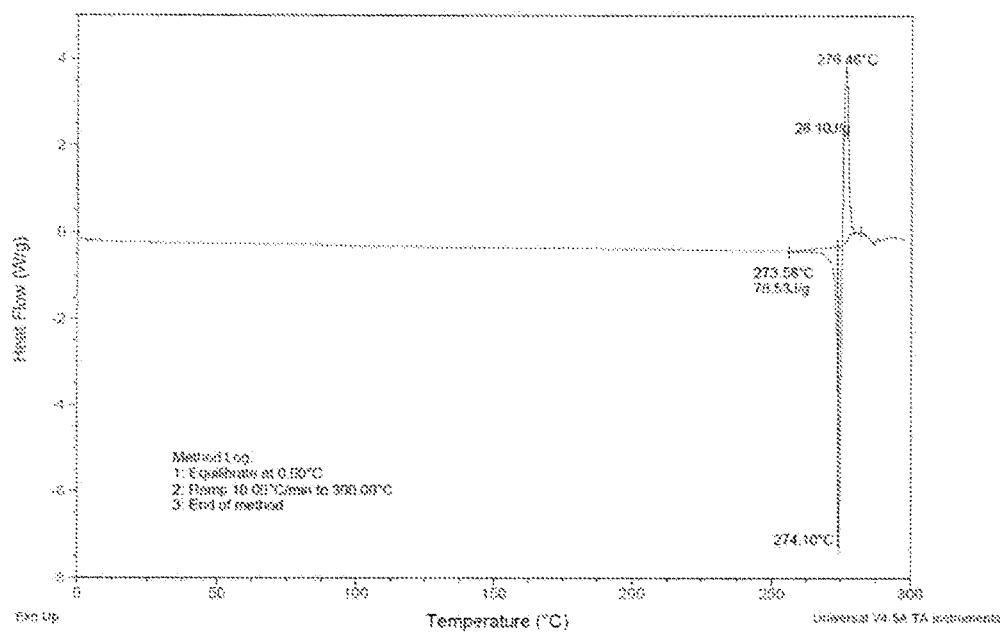
FIG. 2 shows the DSC diagram for the compound of Example 1.

|  | HPLC (% Example 1) | XR | DSC |
|---|---|---|---|
| t = 0 | 99.8% | FIG. 2 | FIG. 1 |
| After 6 months | | | |
| 25° C./60% relative humidity | 99.8% | Diffractogram unchanged | Thermogram unchanged |
| 25° C./90% relative humidity | 99.8% | Diffractogram unchanged | Thermogram unchanged |
| 30° C./65% relative humidity | 99.8% | Diffractogram unchanged | Thermogram unchanged |
| 40° C./75% relative humidity | 99.8% | Diffractogram unchanged | Thermogram unchanged |
| 50° C. | 99.8% | Diffractogram unchanged | Thermogram unchanged |

EXAMPLE 3

Solubility of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione Methanesulphonate, Z Isomer A solution containing 140 mg of the compound obtained in Example 1 in 7 ml of water is stirred for 24 hours at ambient temperature. After filtration using an Acrodisc GHP 0.45° μm, the solution is analysed by HPLC. The solubility of the compound of Example 1 is 14.7 mg/ml (or 12.1 mg/ml in terms of the base equivalent).

Under the same conditions, the solubility of the hydrochloride of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione, Z isomer, is 4.3 mg/ml (or 4 mg/ml in terms of the base equivalent).

EXAMPLE 4

Dissolution Kinetics, at pH 2 (Gastric pH), of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione Methanesulphonate, Z Isomer The constant surface area dissolution kinetics (or intrinsic dissolution kinetics) of the product of Example 1 were determined at ambient temperature at pH 2 (10 mL of 0.01N HCl) using a μDiss dissolution apparatus and pellets of 0.075 cm$^2$, prepared by compression at 90 bars, for 2 minutes at a stirring speed of 100 rpm.

The product of Example 1 dissolves with kinetics of 23 μg·s$^{-1}$·cm$^{-2}$+/−11%. By way of comparison, the dissolution kinetics of the corresponding hydrochloride are 1.6 μg·s$^{-1}$·cm$^{-2}$. The methanesulphonate therefore dissolves about 14 times faster than the corresponding hydrochloride.

EXAMPLE 5

Pharmaceutical Compositions

| 1000 tablets each containing a dose of 5 mg of 3-[3-{[4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate, Z isomer (Example 1) | 5 g |
|---|---|
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. Z isomer of 3-[(3-{[4-(4-Morpholinylmethyl)-1H-pyrrol-2-yl]methylene}-2-oxo-2,3-dihydro-1H-indol-5-yl)methyl]-1,3-thiazolidine-2,4-dione methanesulphonate of formula (II):

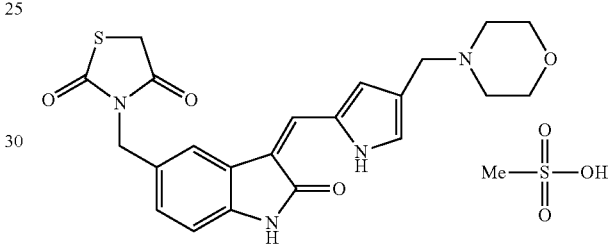

(II)

having an X-ray powder diffractogram which exhibits the Bragg's angles 2 theta (expressed in terms of °+0.2) 12.86; 15.13; 15.50; 17.70; 18.25; 18.71; 20.11; 21.46; 21.67; 21.89; 22.29; 22.58; 24.57; 25.82; 26.33.

2. The compound according to claim 1, which exhibits the following crystal parameters, obtained starting from the powder diffractogram carried out on a Panalytical Xpert-Pro MPD diffractometer (copper anticathode) in transmission mode with an angular range of 3-55° in terms of 2θ, a step of 0.017° and 35.5 s per step:
   unit cell parameters: a=15.0958(5) Å, b=18.4586(6) Å, c=8.8269(2) Å, β=94.074(1)°, γ=90°
   space group: C 1 c 1 (9)
   volume of unit cell: $V_{unit\ cell}$=2453.37600 Å$^3$.

3. A process for obtaining the compound of formula (II) according to claim 1, wherein 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione is dissolved in a binary system of solvent/water, to which solution from 1 to 2 molar equivalents of methanesulphonic acid are added, stirring until the methanesulphonate precipitates out, which precipitate is filtered off.

4. A process for obtaining the compound of formula (II) according to claim 1, wherein 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione hydrochloride is dissolved in a binary system of solvent/water, the pH of which solution is brought to 8 by adding a base, the resulting salt is removed by filtration, the filtrate is then heated and methanesulphonic acid added, and the medium is stirred and cooled until the methanesulphonate precipitates out, which precipitate is filtered off.

5. A pharmaceutical composition comprising the compound of formula (II) according to claim 1 in combination with one or more pharmaceutically acceptable excipients.

6. A method of treating a condition selected from cancers of the colon, breast, liver, kidneys, brain and œsophagus, melanomas, myelomas, ovarian cancers, non-small-cell lung cancers, small-cell lung cancers, prostate and pancreatic cancers, and sarcomas in a subject in need thereof, comprising administration of a compound of formula II according to claim 1 to the subject, optionally in combination with one or more pharmaceutically acceptable excipients.

7. A combination of the compound of formula (II) according to claim 1 with an anti-cancer agent selected from genotoxic agents, mitotic poisons, anti-metabolites, proteasome inhibitors and kinase inhibitors.

8. A method of treating cancer in a subject in need thereof, comprising administration of a combination according to claim 7 to the subject.

9. A method of treating cancer in a subject in need thereof, comprising administration of a compound of formula (H) according to claim 1 to the subject in combination with radiotherapy.

\* \* \* \* \*

UNITED STATES PATENT AND TRADEMARK OFFICE
CERTIFICATE OF CORRECTION

PATENT NO. : 9,925,195 B2
APPLICATION NO. : 14/904260
DATED : March 27, 2018
INVENTOR(S) : Alexandre Le Flohic, Jérôme Guidotti and Philippe Letellier Page 1 of 1

It is certified that error appears in the above-identified patent and that said Letters Patent is hereby corrected as shown below:

On the Title Page

Title: "SALT OF 3-[(3-{[4-(4-MORPHOLINYLMETHYL)-1H-PYRROL-2-YL]
METHYLENE}-2-OXO-2,3-DIHYDRO-1H-INDOL-5-YL)METHYL]-1,3-THIAZOLIDINE-2,4-
DIONE, ITS PREPARATION, AND FORMULATIONS CONTAINING I" should be
--SALT OF 3-[(3-{[4-(4-MORPHOLINYLMETHYL)-1H-PYRROL-2-YL]
METHYLENE}-2-OXO-2,3-DIHYDRO-1H-INDOL-5-YL)METHYL]-1,3-THIAZOLIDINE-2,4-
DIONE, ITS PREPARATION, AND FORMULATIONS CONTAINING IT--.

In the Claims

Column 7, Line 20: "formula (H)" should be --formula (II)--.

Signed and Sealed this
Eighth Day of May, 2018

Andrei Iancu
*Director of the United States Patent and Trademark Office*